(12) United States Patent
Avitall

(10) Patent No.: US 8,998,893 B2
(45) Date of Patent: Apr. 7, 2015

(54) CATHETER SYSTEMS FOR CARDIAC ARRHYTHMIA ABLATION

(76) Inventor: Boaz Avitall, Whitefish Bay, WI (US)

( * ) Notice: Subject to any disclaimer, the term of this patent is extended or adjusted under 35 U.S.C. 154(b) by 946 days.

(21) Appl. No.: 13/106,309

(22) Filed: May 12, 2011

(65) Prior Publication Data
US 2012/0143179 A1 Jun. 7, 2012

Related U.S. Application Data

(63) Continuation-in-part of application No. 12/961,781, filed on Dec. 7, 2010.

(51) Int. Cl.
A61B 18/12 (2006.01)
A61B 18/14 (2006.01)
A61B 5/042 (2006.01)
A61B 18/02 (2006.01)
A61B 18/00 (2006.01)
A61B 19/00 (2006.01)
A61B 5/00 (2006.01)

(52) U.S. Cl.
CPC ............ *A61B 18/1492* (2013.01); *A61B 5/042* (2013.01); *A61B 18/02* (2013.01); *A61B 2018/00011* (2013.01); *A61B 2018/00023* (2013.01); *A61B 2018/0022* (2013.01); *A61B 2018/00357* (2013.01); *A61B 2018/00375* (2013.01); *A61B 2018/00577* (2013.01); *A61B 2018/00791* (2013.01); *A61B 2018/00815* (2013.01); *A61B 2018/00875* (2013.01); *A61B 2018/124* (2013.01); *A61B 2018/1407* (2013.01); *A61B 2019/465* (2013.01); *A61B 5/6853* (2013.01)

(58) Field of Classification Search
USPC .............................. 606/27, 34, 41
See application file for complete search history.

(56) References Cited

U.S. PATENT DOCUMENTS

| 4,998,933 | A | * | 3/1991 | Eggers et al. ............... 606/41 |
|---|---|---|---|---|
| 5,311,866 | A | * | 5/1994 | Kagan et al. ............... 600/374 |
| 5,776,129 | A | | 7/1998 | Mersch |
| 5,800,482 | A | | 9/1998 | Pomeranz et al. |
| 5,836,947 | A | | 11/1998 | Fleischman et al. |
| 6,012,457 | A | | 1/2000 | Lesh |
| 6,033,397 | A | * | 3/2000 | Laufer et al. ............... 606/27 |
| 6,071,274 | A | * | 6/2000 | Thompson et al. .......... 604/528 |
| 6,217,528 | B1 | | 4/2001 | Koblish et al. |
| 6,258,087 | B1 | * | 7/2001 | Edwards et al. ............. 606/41 |
| 6,322,559 | B1 | * | 11/2001 | Daulton et al. ............. 606/41 |
| 6,430,426 | B2 | | 8/2002 | Avitall |

(Continued)

FOREIGN PATENT DOCUMENTS

WO WO02/17804 3/2002
WO WO2010/056771 5/2010

OTHER PUBLICATIONS

Notification of Transmittal of the International Search Report and the Written Opinion of the International Searching Authority, or the Declaration; the International Search Report mailed Jul. 25, 2012; the Written Opinion mailed Jul. 25, 2012.

*Primary Examiner* — Michael Peffley
*Assistant Examiner* — Daniel Fowler
(74) *Attorney, Agent, or Firm* — Nikolai & Mersereau, P.A.; C. G. Mersereau

(57) ABSTRACT

A plurality of catheter-based ablation apparatus embodiments are provided that address several areas of atrial target tissue and which feature firm and consistent ablation element to tissue contact enabling the creation of effective continuous lesions.

16 Claims, 11 Drawing Sheets

(56) References Cited

U.S. PATENT DOCUMENTS

| | | | |
|---|---|---|---|
| 6,475,213 | B1 | 11/2002 | Swanson et al. |
| 6,502,576 | B1 | 1/2003 | Lesh |
| 6,514,249 | B1 | 2/2003 | Maguire et al. |
| 6,638,276 | B2 * | 10/2003 | Sharkey et al. ............ 606/41 |
| 6,640,138 | B1 | 10/2003 | Schaefermeyer et al. |
| 6,666,858 | B2 * | 12/2003 | Lafontaine ............ 606/21 |
| 6,855,144 | B2 | 2/2005 | Lesh |
| 7,025,766 | B2 | 4/2006 | Whayne et al. |
| 7,104,990 | B2 * | 9/2006 | Jenkins et al. ............ 606/49 |
| 7,175,619 | B2 | 2/2007 | Koblish et al. |
| 7,429,261 | B2 | 9/2008 | Kunis et al. |
| 7,468,062 | B2 | 12/2008 | Oral et al. |
| 7,678,108 | B2 | 3/2010 | Chrisitian et al. |
| 8,080,006 | B2 | 12/2011 | Lafontaine et al. |
| 8,216,216 | B2 | 7/2012 | Warnking et al. |
| 2003/0014049 | A1 | 1/2003 | Koblish et al. |
| 2003/0093069 | A1 | 5/2003 | Panescu et al. |
| 2003/0199861 | A1 | 10/2003 | Lafontaine |
| 2004/0143249 | A1 | 7/2004 | Lafontaine |
| 2004/0181139 | A1 * | 9/2004 | Falwell et al. ............ 600/374 |
| 2004/0193239 | A1 | 9/2004 | Falwell et al. |
| 2005/0096647 | A1 * | 5/2005 | Steinke et al. ............ 606/41 |
| 2005/0183732 | A1 * | 8/2005 | Edwards ............ 128/898 |
| 2005/0240116 | A1 | 10/2005 | Saadat et al. |
| 2006/0004353 | A1 * | 1/2006 | Koyfman et al. ............ 606/41 |
| 2007/0255162 | A1 | 11/2007 | Abboud et al. |
| 2008/0033241 | A1 * | 2/2008 | Peh et al. ............ 600/109 |
| 2008/0281312 | A1 | 11/2008 | Werneth et al. |
| 2008/0281322 | A1 | 11/2008 | Sherman et al. |
| 2008/0312643 | A1 | 12/2008 | Kania et al. |
| 2009/0018534 | A1 | 1/2009 | Taimisto et al. |
| 2009/0299355 | A1 | 12/2009 | Bencini et al. |

* cited by examiner

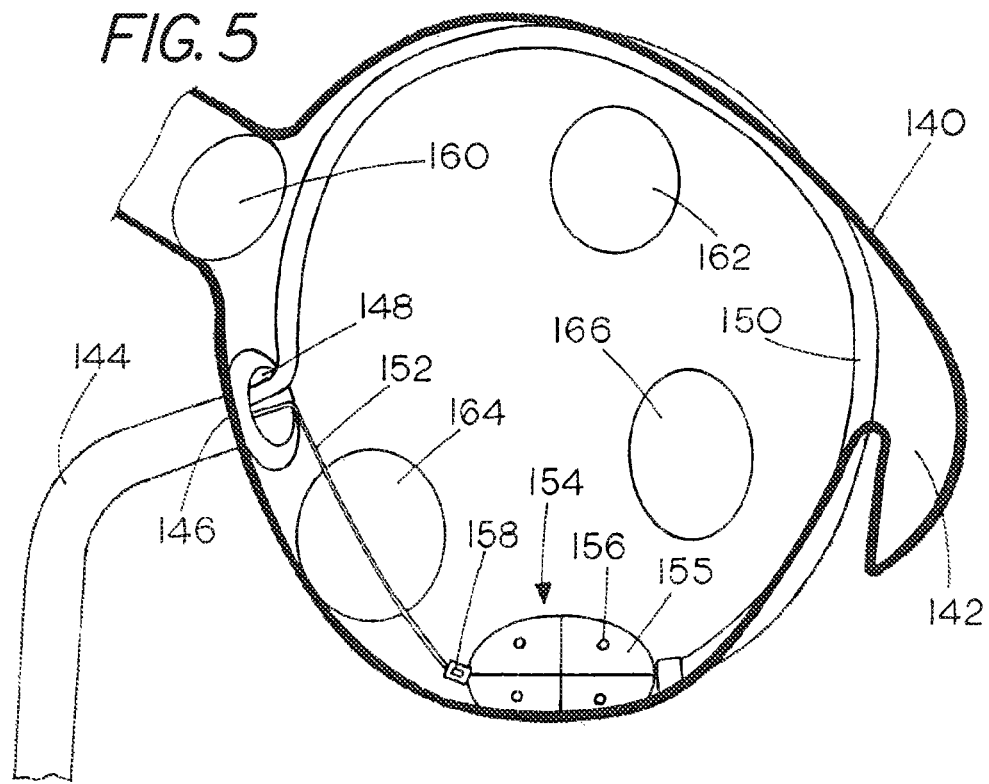
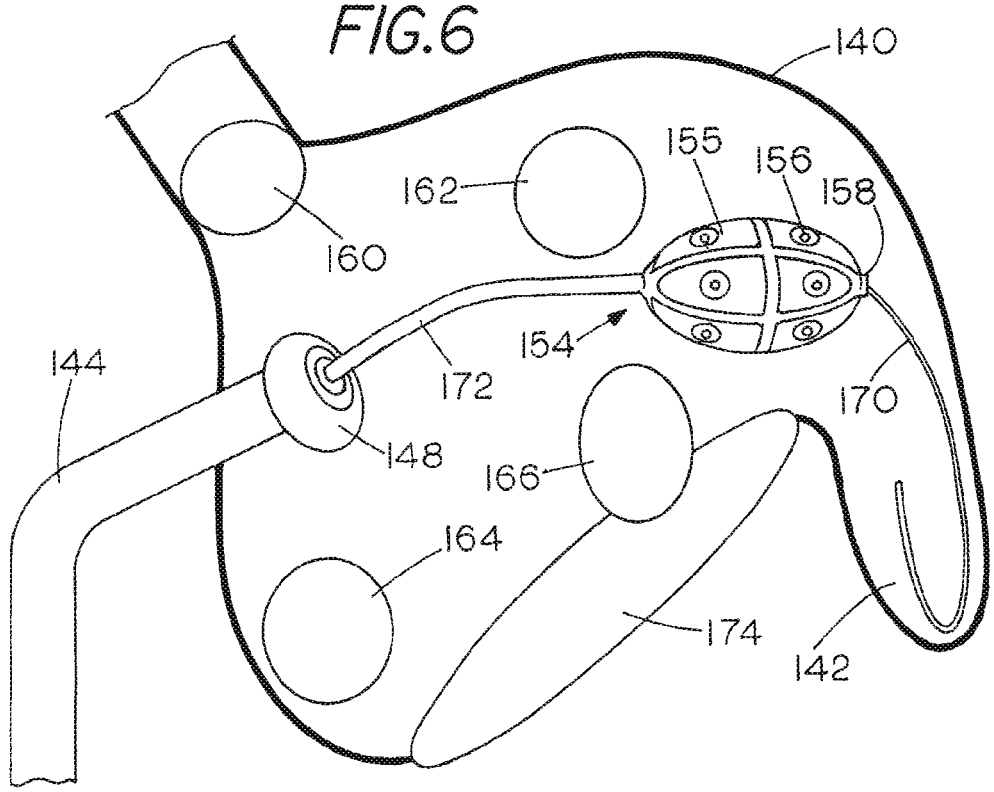

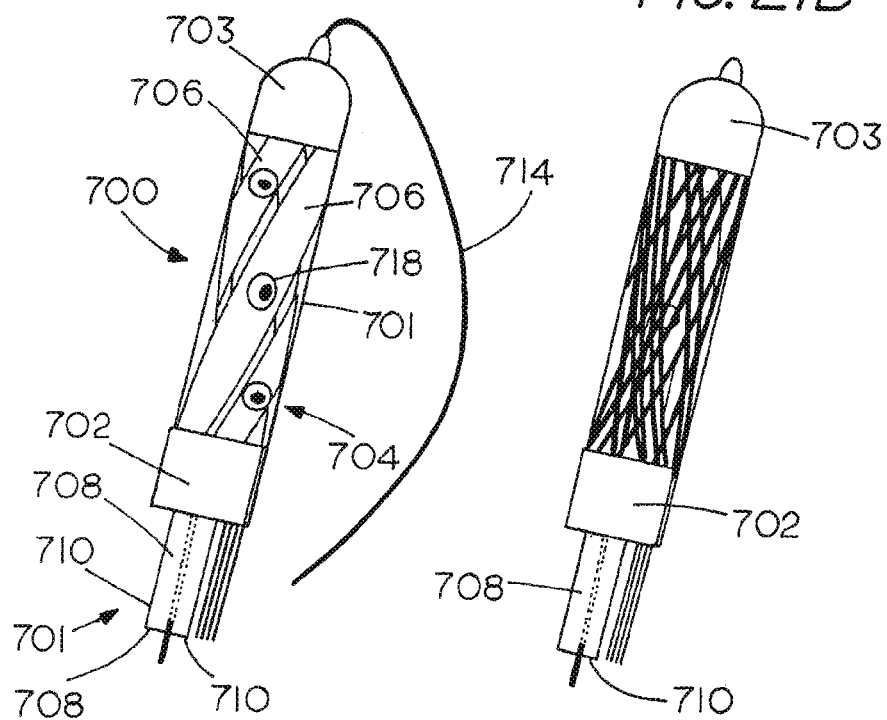
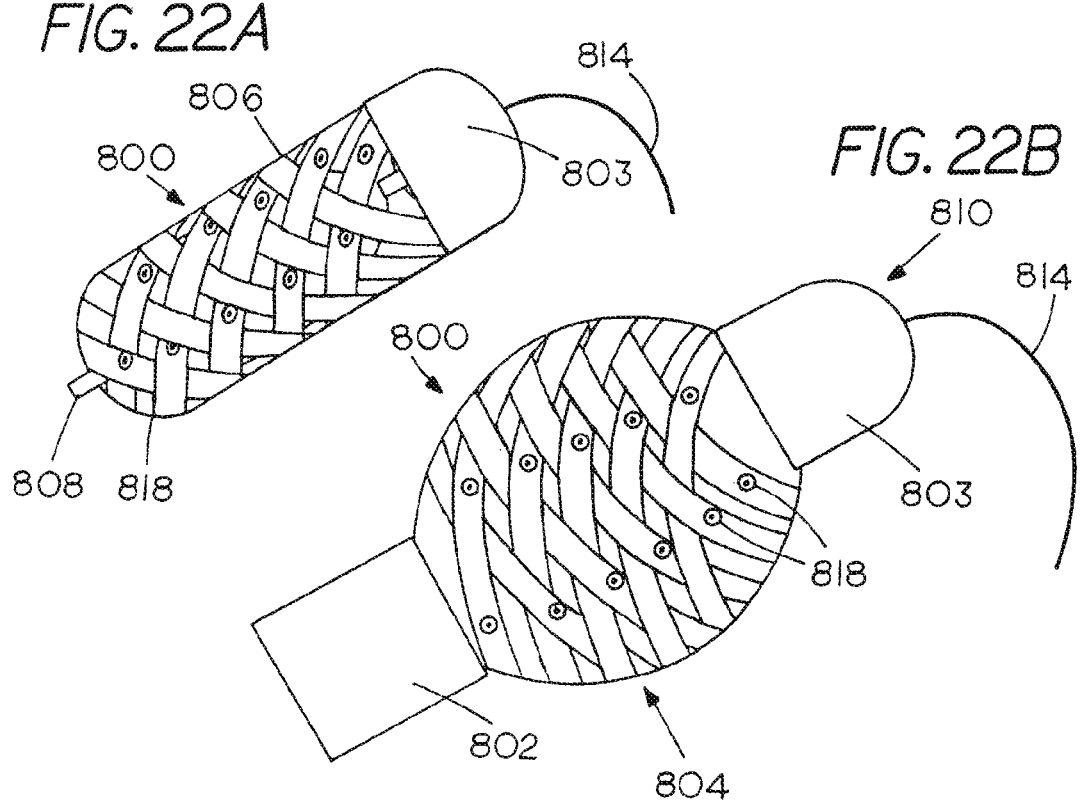

CATHETER SYSTEMS FOR CARDIAC ARRHYTHMIA ABLATION

CROSS-REFERENCE TO RELATED APPLICATIONS

This application is a continuation-in-part of application Ser. No. 12/961,781, filed Dec. 7, 2010, entitled "CATHETER SYSTEMS FOR CARDIAC ARRHYTHMIA ABLATION", which is deemed incorporated herein by reference in its entirety.

STATEMENT REGARDING FEDERALLY SPONSORED RESEARCH OR DEVELOPMENT

Not applicable.

BACKGROUND OF THE INVENTION

I. Field of the Invention

The present invention relates generally to the field of catheter-based tissue ablation devices and techniques and, more particularly, to systems for ablation to relieve atrial cardiac arrhythmias. Specifically, the invention relates to curing atrial fibrillation by using transcutaneous transvascular catheter ablation to recreate the effect of the Cox Maze surgical procedure.

II. Related Art

Cardiac arrhythmias, particularly atrial fibrillation, are common and dangerous medical conditions causing abnormal, erratic cardiac function. Atrial fibrillation is observed particularly in elderly patients and results from abnormal conduction and automaticity in regions of cardiac tissue. Chronic atrial fibrillation (AF) may lead to serious conditions including stroke, heart failure, fatigue and palpitations. The treatment of chronic AF requires the creation of a number of transmural contiguous linear lesions. The use of a pattern of surgical incisions and thus surgical scars to block abnormal electrical circuits, known as the Cox Maze procedure, has become the standard procedure for effective surgical cure of AF. The procedure requires a series of full-thickness incisions to isolate the pulmonary veins and the posterior wall of the left atria. Additional lines involve the creation of lesions from the posterior wall to the mitral valve, at the atrial isthmus line and superior vena cava (SVC) to the inferior vena cava (IVC) with a connection to the right atrial appendage.

Catheters have been developed that make the corrective procedure less invasive. They are designed to create lesions by ablation of tissue that performs the function of the surgical incisions. These include catheters that attempt to connect a series of local or spot lesions made using single electrodes into linear lesions. Devices that use a linear array of spaced electrodes or electrodes that extend along the length of a catheter have also been proposed.

More recently, technologies regarding cryogenic and radio frequency (RF) balloon devices in addition to loop type multi-electrode catheter devices have been proposed for the isolation of the pulmonary veins (PV). It has been found that isolation of the PVs can be achieved consistently with a PV cryogenic balloon device now in clinical trials. However, presently no technology has been shown to consistently and safely create effective transmural contiguous lesions that exhibit an effectiveness that rivals the surgical cuts placed in the Cox Maze.

Important drawbacks found fundamental in the current approaches can be attributed to several factors including a lack of consistent contact between the ablation devices and the target tissues, an inability to define lesion maturation and the inability to connect lesions in a manner so as to create a continuous transmural line that produces an electrical conduction block.

SUMMARY OF THE INVENTION

In accordance with the present invention a plurality of catheter-based ablation apparatus embodiments are provided that address several areas of atrial target tissue and which feature firm and consistent ablation element-to-tissue contact enabling the creation of effective continuous linear lesions.

The ablation devices of the invention all are extended from the distal portion of a main guide body or deflectable sheath that is capable of penetrating heart septum tissue to enter the desired chamber. Transeptal guide body sheath devices are known to those skilled in the art. The distal portion of the guide body or sheath is preferably further provided with an inflatable balloon device to prevent the sheath from retracting back through the penetrated septum during a procedure. This could result in damage to the septum caused by a protruding guidewire or the like. This protective balloon can be expanded using a benign solution such as saline or saline mixed with contrast for visualization.

Several embodiments of ablation devices of the present concept are in the form of inflatable balloons which are attached to and positioned using an expandable guidewire loop which is anchored at one end in a deflectable catheter sheath. The length of the guidewire loop emanating from the guide body or sheath is adjustable and can be controlled to press with force against and firmly adhere to adjacent atrial tissue. A balloon ablation device is adapted to be advanced over the guidewire in a deflated condition until the balloon is in a desired position along the loop. Once the balloon is properly positioned, it can be expanded and moved and positioned along the guidewire in an expanded state and thereby allow delivery of radio frequency (RF) or cryogenic energies to the targeted tissue for ablation. An end of the guidewire loop or attached pull line fixes the end of the guidewire with respect to the distal end of the sheath. The guidewire loop within the atria can be expanded by inserting additional guidewire into the sheath from a control handle or the loop can be shrunk by retracting guidewire out of the sheath. These actions can be used to control the size and disposition of the guidewire loop.

The balloon embodiments generally may be of two or more types, ones that use radio frequency (RF) energy to ablate tissue with heat and ones that use cryogenics to ablate tissue by freezing. However, other energy forms can be used such as laser energy. Radio frequency (RF) ablation balloons have an outer surface provided with a plurality of segmented RF ablation electrodes and thermistors to measure temperature. RF ablation is closely monitored with respect to RF power, electrode temperature and observance of local electrogram amplitude and percent change. Overheating of ablated tissue may cause serious problems and RF electrodes are preferably cooled during RF application by circulating cooling saline solution or the like which may also contain a contrast material for easier location tracing. The ablation balloon includes several elements that enable determination of its three-dimensional position, tissue temperature and electrical activity (local electrogram) during the ablation process. Pressure and surface temperature can be precisely measured and monitored by imbedded temperature and pressure sensors. The balloon temperature can be controlled by the saline circulation that is used to cool the balloon allowing higher delivered power to create deeper lesions if needed.

Cryogenic balloon embodiments are also designed to be delivered over a guidewire delivery and tracking system. The cryogenic balloon preferably consists of two concentric balloons, an inner and an outer balloon. The inner balloon is adapted to receive and contain the cryogenic fluid, normally liquid nitrous oxide ($N_2O$) under pressure and the outer balloon is filled with a low pressure insulating gas highly absorbable in blood such as nitrogen ($N_2$) or carbon dioxide ($CO_2$) at a pressure just above the normal pressure in the atria. In this manner, the outer balloon serves to insulate the cryogenic fluid in the inner balloon from the warm atrial blood flow, thus reducing the effects on the blood and allowing much of the cryogenic power to be directed to the targeted tissues.

Expansion of the relatively stiff guidewire loop forces the inner balloon toward and against the tissue resulting in displacement of the insulating gas in the outer balloon where the tissue is engaged causing the two balloons to be in firm contact with each other and the tissue, thus allowing maximal freezing effect to be directed into the tissues of interest at that interface. In addition, two ring electrodes may be preferably placed on the distal and proximal end allowing both electrical recording and positioning of the catheter using presently known 3D guiding systems. In addition, as mentioned above, embedded thermistors and additional electrical recording electrodes can be painted on the surface of the outer balloon and used for cardiac electrical mapping, and lesion assessment. A simpler embodiment may consist of a single layer cryogenic balloon with segmented painted surface electrodes and thermistors.

An additional anchoring approach involves embedding a soft distal portion of a stiff guidewire in the left atrial appendage and tracking the ablation balloon over the guidewire to create linear lesions. The same type of RF ablation catheter can be guided by the same or similar guidewire into the PVs for the creation of circumferential PV isolation lesions.

By means of the invention, there is also provided embodiments of a catheter system that use the pulmonary vein (PV) entrances as base anchors for a multi-electrode system for the creation of linear lesions between the pulmonary veins (PVs). These linear lesions are needed to electrically isolate the posterior wall of the left atrium between the PVs, an area that has been shown to be an active driver of atrial fibrillation (AF).

The pulmonary vein anchored embodiments include a transeptal sheath, nominally a 10-11F sheath, used to cross the atrial septum and access the left atrium. Two additional sheaths are placed inside the transeptal sheath which are configured with fixed deflections that allow insertion of each of the sheaths into a PV. These sheaths provide the anchors and support for a multi-electrode catheter ablation segment that forms a bridge between the supporting sheaths. By stretching the ablation-electroded segment of the catheter, a good tissue contact is formed and a transmural and contiguous lesion can be placed between pulmonary veins. By placing the support sheath anchors in different PVs, linear lesions between all of the PVs can be created. These lesions are normally additional lesions that are placed after isolation of the PVs by either RF or cryogenic balloon lesions are provided, as described above. These embodiments have an advantage since they allow for force to be applied to the catheter at the tissue interface, thereby creating good ablation electrode and tissue contact ensuring a good lesion.

In an additional embodiment the ablation catheter is placed within a guiding deflectable sheath and by pushing the catheter into the sheath a rigid loop is created which moved to create contact with the tissues by moving or deflecting the guide sheath. To minimize the size of the guide sheath one side of the ablation catheter can be flexibly attached to the end of the sheath and thereafter adjusting the catheter into and out of the sheath creates an expanding loop. Another option is to insert the ablation catheter into the sheath with a pull string attached to the distal end of the catheter. Once the catheter is in the desired chamber, the pull string can be retracted to bring the end of the multi-electrode ablation catheter against the tip of the sheath to create a loop by pushing the proximal end of the ablation catheter into the sheath.

An electrically insulated extension rod can be attached to the ablation electrode array to further assist with the loop expansion and tissue contact.

The balloon catheters of the present invention can also be combined with an attached J-loop shaped PV recording and impedance measuring catheter segment provided with recording and stimulation electrodes to record electrical activity and verify pulmonary vein (PV) isolation and lesion quality.

The last embodiment allows the radio frequency generator to direct the RF application to the electrode that are in firm contact with the tissues and titrate the power application time based on the tissue viability. This approach to the ablation will prevent extracardiac tissue damage while insuring lesion maturation.

BRIEF DESCRIPTION OF THE DRAWINGS

In the drawing figures:

FIG. 5 is a schematic representation of an RF or cryogenic balloon ablation device as positioned in the left atrium using a loop guidewire for the creation of a circumferential lesion;

FIG. 6 is a schematic representation depicting an RF or cryogenic balloon ablation device using an anchoring guidewire anchored in the left atrium appendage;

FIGS. 21A and 21B are schematic representations of a slightly different embodiment of an RF balloon ablation device having a slanted electrode configuration; and FIGS. 22A and 22B are schematic representations of another variation of a balloon ablation device shown in a collapsed and expanded state, respectively.

DETAILED DESCRIPTION

The following detailed description pertains to several embodiments that include concepts of the present development. Those embodiments are meant as examples and are not intended to limit the scope of the present invention in any manner.

It will be appreciated that the present development contemplates a less invasive yet comparably effective solution to atrial fibrillation that replaces the surgical lesions of the traditional Cox Maze with lesions created by tissue ablation using catheters which avoids the need for radical surgical procedures. The ablation devices of the invention provide firm and consistent ablation surface to tissue contact.

Figure 1:
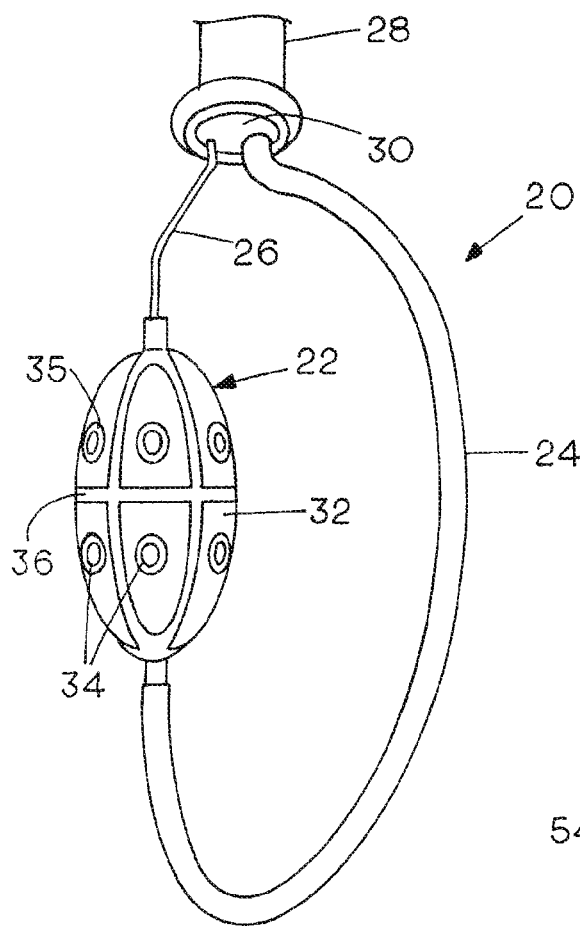
FIG. 1 is a schematic representation of an embodiment including a radio frequency (RF) balloon ablation device with segmented electrodes controlled by an adjustable loop guidewire system.
Figure 3:
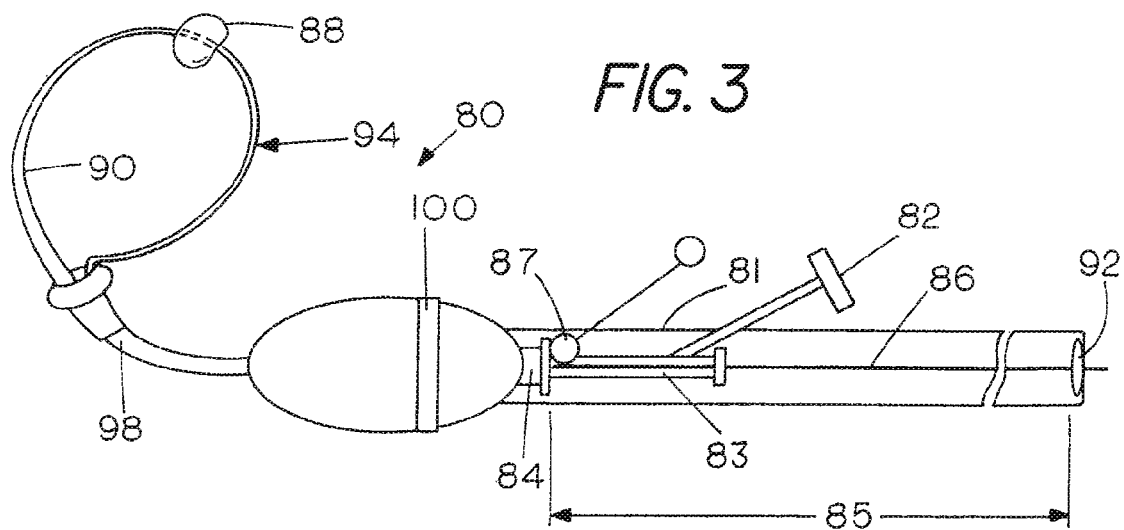
FIG. 3 is a partial schematic representation depicting a balloon ablation device with a control handle suitable for use with the balloon ablation catheter devices of the invention.

FIG. 1 is a schematic representation of an embodiment of an RF balloon ablation device generally depicted by the reference character 20. The ablation device includes an ablation balloon 22, shown as inflated, mounted on a flexible catheter shaft 24 that may be a 7F flexible catheter guide shaft that is about 4 feet (122 cm) long. All of the ablation control and data measurement conductors or wires are embedded in the shaft wall that rides over a guidewire 26. The most distal section of the guidewire 26 is about 2 cm long and is of a relatively soft, flexible, material, which is softer and more flexible than the remainder of the loop, which is relatively stiff. The guidewire may be attached to or drawn through the distal end of a deflectable transdermal sheath, a fragment of which is shown at 28. A transeptal breach protection balloon, which is inflated, normally with saline to prevent undesirable withdrawal of the sheath 28 during a procedure, is shown at 30. The position of the catheter can be adjusted by moving the adjustable shaft 24 relative to the guidewire 26 using a proximal handle control as shown in FIG. 3.

The balloon 22 further includes a plurality of segmented conductive painted RF electrodes 32, each of which is provided with a centrally located recording electrode for sensing electrical activity and a combined recording and thermistor elements 34 for sensing temperature. The electrodes are highly conductive paintings on the balloon surface and can be selectively and separately energized and sensed in a well known manner. While the balloon itself may be any convenient size, a typical embodiment will be about 25-30 mm long by 15 mm in diameter when fully inflated. Such balloons may be made of any suitable benign coatable polymer material that maintains stable inflated dimensions and is constructed to include separated conductive segments for tissue ablation, thermistors placed at the center of each ablation electrode as well as a recording electrode. One such preferred material is polyethylene terphthalate (PET), and it is believed that other suitable materials could be used.

As indicated, the RF balloon is coated with a highly conductive compound painted on the balloon in electrode segments 32 as shown in FIG. 1. The balloon of one typical preferred embodiment measures about 30 mm in length and has a diameter of about 15 mm. The balloon preferably has eight segmented conductive painted electrode segments 32 separated by non-conducting bands, as at 36, which may be about 1.5 mm wide. The combined recording and thermistor elements are generally about 2 mm in diameter and are separated from the conductive segments 32 by a 1 mm insulating outer ring 35. The recording electrodes and thermistors, located generally at the center of each ablation element, monitor the pre and post ablation electrical activity and monitor temperature. The RF ablation balloon is preferably filled with saline mixed with low concentration of contrast fluid under low pressure. The saline is circulated inside the balloon while maintaining constant inner balloon pressure to keep the balloon itself cool and allow for more effective ablation.

Figure 2:
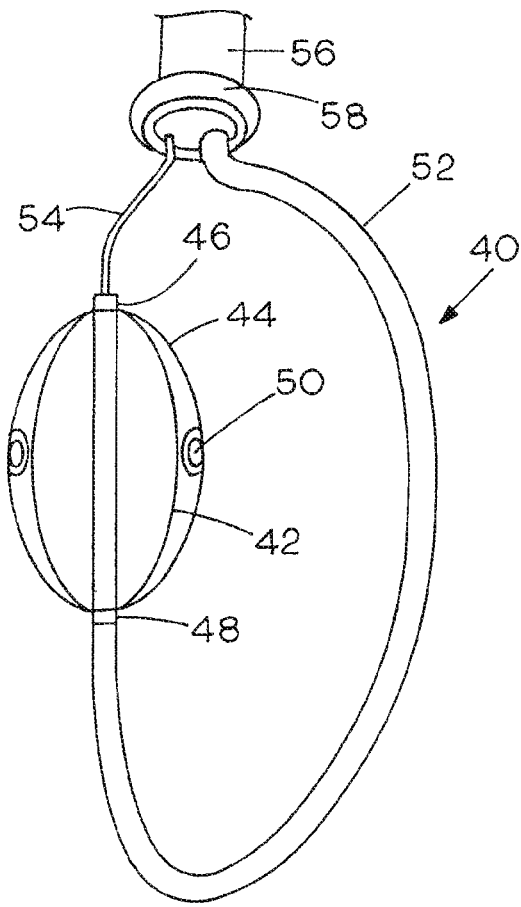
FIG. 2 is a schematic representation that depicts an embodiment including a cryogenic balloon ablation device having inner and outer concentric balloons that travel along an adjustable loop guidewire.

FIG. 2 depicts an embodiment of a cryogenic ablation device in accordance with the invention that uses a dual balloon system including both a cryogenic balloon and a low pressure insulating balloon for thermal insulation. The dual balloon construction includes an inner cryogenic balloon 42 and an outer insulating balloon 44. Ring electrodes 46 and 48 are located at the distal and proximal ends of the balloon, respectively, to provide electrical activity recording and positional verification. Embedded thermistors and recording electrodes, represented at 50, are also located at desired points on the outer balloon and connected in a well known manner. The balloon device is mounted on a flexible catheter guide shaft 52 that rides over the guidewire 54. As was the case with the RF device, the position of the balloon can be changed by pulling or pushing the balloon catheter guide shaft over the guidewire. The recording electrodes enable cardiac electrical mapping and lesion assessment. The deployment system may be similar to that for the RF balloon shown in FIG. 1. Thus, a guidewire loop is shown at 54 with relatively soft flexible section which may be attached through the end of a deflectable sheath 56 attached to a pull cord (not shown). Sheath 56 includes a transeptal protection balloon at 58.

In the two balloon cryogenic systems, the inner balloon receives and contains a cryogenic liquefied material which may be liquid nitrous oxide ($N_2O$), which boils at −88.5° C., and the outer balloon is filled with an insulating gas such as $CO_2$ or $N_2$ at a pressure just above the left atrial pressure. In this manner, the cryogenic liquid gas is normally insulated from the inner atrial blood flow. During ablation, expansion of the guidewire loop is used to force the balloon towards the tissue at locations of interest and the force displaces the insulating gas in the area of tissue contact thereby enabling the cryogenic inner balloon to come into firm contact with the outer balloon which produces maximum heat transfer between the balloon and the tissue resulting in maximum local tissue freezing.

A control handle is provided (FIG. 3) to advance the balloon shaft over the guidewire and adjust its position on the guidewire as illustrated in FIGS. 4A-4E.

FIG. 3 shows a schematic representation of an embodiment of a balloon catheter ablation system generally at 80 including a flat control handle member 81 that includes an RF/cryogen connector 82 for applying fluid materials to a balloon 88. An ablation (RF/cryogen) balloon catheter having a proximal end catheter shaft gliding or operating handle 83 is shown extending into a guide sheath 84. The proximal end handle 83 is the proximal end of the balloon ablation catheter shown at 90. The catheter is slidably mounted over the guidewire 86 and both are delivered to the atria, or other chamber, via the guide sheath 84. The ablation balloon catheter shaft is inserted into the deflectable sheath over the relatively stiff portion of the guidewire. The relatively soft portion of the guidewire is extended from the sheath and can be locked in place to prevent the guidewire from drifting or moving further into the sheath when the balloon catheter is moved along the guidewire. To accomplish this, a movable locking device represented at 87 is provided. The position of the balloon along the guidewire loop can be changed by moving the catheter proximal end handle 83 along and over the guidewire section 86. A guidewire fixation lock is shown at 92. It allows a variable length guidewire fixation point to vary the size of the projected loop and allow the ablation balloon to cover additional distance. The ablation balloon catheter sliding range over adjustable guidewire loop 94 as controlled by handle 83 is indicated by the arrow 85. A deflectable sheath section is shown at 98 and with soft flexible guidewire loop segment at 94. A sheath deflection ring is shown at 100.

Figure 4A:
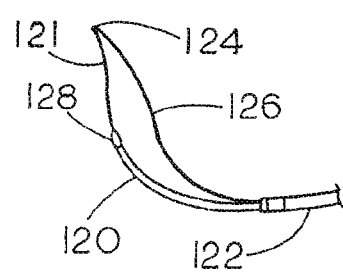
FIGS. 4A-4E show different positions of the ablation balloon device and a variety of shapes and loops that can be created by the adjustable guidewire with a pull line.
Figure 4B:
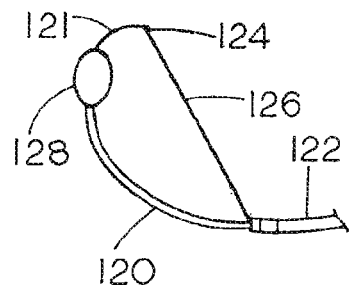
Figure 4C:
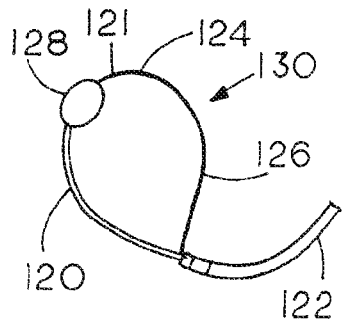
Figure 4D:
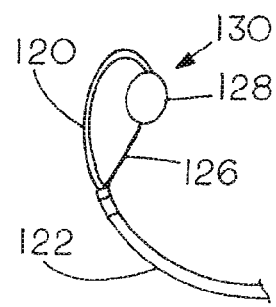
Figure 4E:
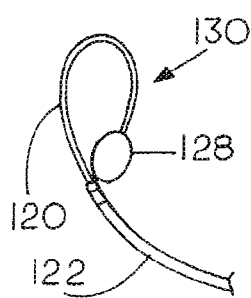

The five panels of FIGS. 4A-4E show an ablation catheter shaft 120 advanced over a guidewire 121 from inside a deflectable sheath 122. The distal end of the guidewire at 124 is attached to a pull line or pull wire 126 which is controlled from a control handle (not shown). A balloon ablation device that has been advanced over the guidewire is shown at 128. The ablation device is shown in a deflated condition in FIG. 4A. In this condition, the deflectable guide sheath has already penetrated into the left atria or other chamber. In FIG. 4B, the balloon is inflated and the pull wire 126 is shown drawing the end of the guidewire 124 toward the sheath thereby creating a guidewire loop. In FIG. 4C, the end of the guidewire has been pulled back inside of the sheath creating a loop 130. FIGS. 4D and 4E show how the size of the loop 130 can be adjusted by advancing or retracting the guidewire in the sheath. The position of the balloon 128 over the guidewire can also be adjusted as shown in 4D to 4E by advancement or retraction of the ablation balloon shaft 83 (FIG. 3) over the guidewire.

FIG. 5 is a schematic diagram showing how an ablation balloon guided by an adjustable loop guidewire in the left atrium can create circumferential lesions. Thus, the wall of the left atrium is represented by 140 with the left atrial appendage shown at 142. A transeptal guide sheath 144 is shown penetrating the septum between the right and left atria at 146. The sheath includes an integral inflatable balloon 148 filled with saline which protects the septum from tearing at the transeptal breach during the procedure. The balloon catheter shaft is shown at 150 and the guidewire with flexible segment at 152. The segmented ablation balloon, which can be either a radio frequency or cryogenic ablation device, is shown at 154 with thermistors and recording electrodes shown in each balloon surface segment 155 as at 156. Further, ring electrodes are provided on each end of the balloon, one of which is shown at 158. The diagram further shows the location of the outlets of the pulmonary veins, including the right superior pulmonary vein (RSPV) 160, left superior pulmonary vein (LSPV) 162, right inferior pulmonary vein (RIPV) 164 and left inferior pulmonary vein (LIPV) 166.

As will be noted in conjunction with FIG. 5, the segmented ablation balloon 154 is held tightly against the wall of the left atrium 140 by the guidewire loop. By adjusting the size of the guidewire loop by inserting more guidewire as needed and adjusting the position of the ablation balloon 154 by increments along the guidewire loop, it can be seen that a complete continuous circumferential lesion can be created in the left atrium.

FIG. 6 is a view similar to FIG. 5 showing an alternative system for anchoring the segmented painted ablation balloon 154 in which, instead of the loop system, an anchoring soft portion of a relatively stiff guidewire 170 is provided to be embedded in the left atrial appendage 142 and the ablation balloon thereafter may be tracked over the guidewire 170 to create the linear lesions about the left atrium. The mitral valve is indicated at 174.

Figure 7:
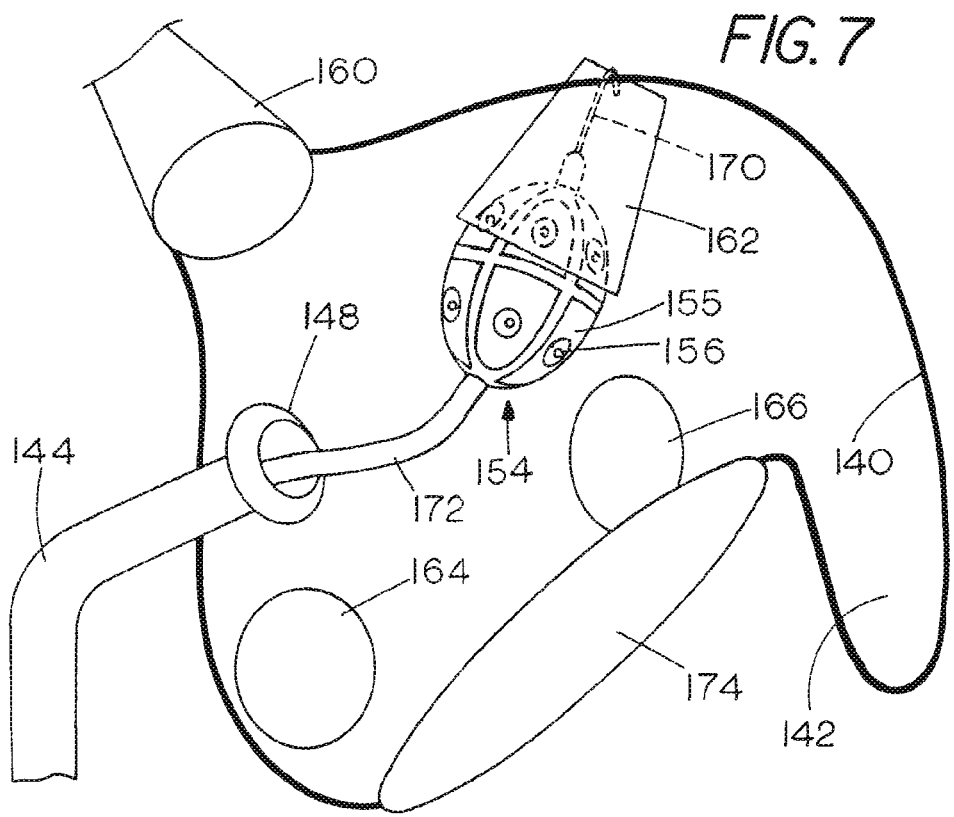
FIG. 7 is a schematic diagram showing an RF or cryogenic ablation balloon with segmented electrodes and thermistors guided by a guidewire in the left superior pulmonary vein (LSPV) for the creation of a pulmonary vein (PV) isolation lesion.

FIG. 7 is a schematic representation similar to FIG. 6 showing the segmented painted ablation balloon 154 situated in the orifice or antrum area just beyond the orifice of the LSPV 162 where it can be used for the creation of a pulmonary vein isolation lesion. In this manner, each of the pulmonary veins can be treated to create a pulmonary vein isolation lesion.

Figure 8:
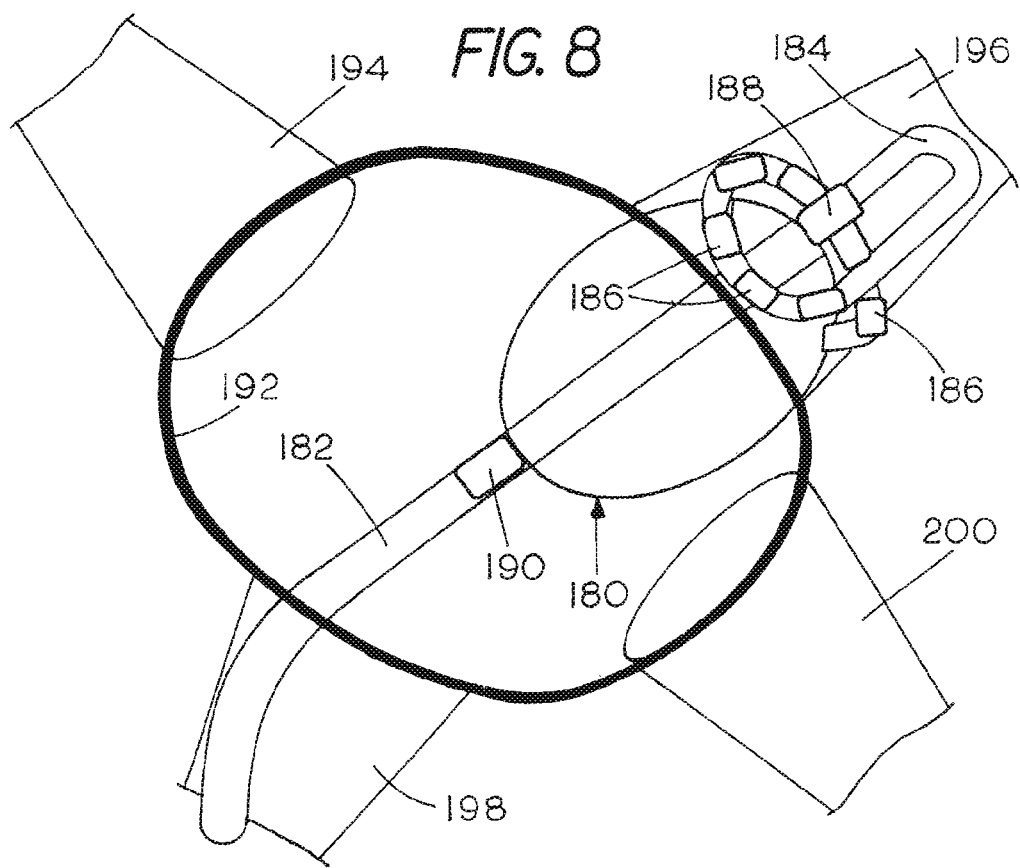
FIG. 8 is a schematic representation of a balloon catheter combined with a J-loop pulmonary vein recording and impedance measurement catheter device capable of measuring PV occlusion and lesion quality, maturation and electrical isolation.

FIG. 8 is a schematic diagram showing a radiofrequency or cryogenic balloon 180 that is shown inserted in the orifice of the LSPV 196. The balloon is guided into the PV by the transeptal sheath 182 and the J type 4F loop recording catheter 184. The J loop includes an array of recording and stimulation electrodes 186 and the balloon is further provided with a distal ring electrode 188 and a proximal ring electrode 190 for the measurement of impedance during the ablation (specifically when using the cryogenic balloon) procedure to define pulmonary vein occlusion and thereafter lesion quality. The atrial wall is shown at 192 and the pulmonary veins are indicated by 194, 196, 198 and 200. For use with the embodiment of FIG. 8, the balloon catheter 180 can be constructed in the same manner as those shown in FIGS. 6 and 7. If the catheter is a cryogenic device, an ice ball is created during the ablation process and recording and impedance measurements across the ice ball that is created during cryogenic ablation allows verification of the ice ball size lesion completion and ablation efficacy.

It will be appreciated that the J-type loop PV recording, stimulation and impedance measurement catheter in combination with the balloon ablation device can realize PV isolation with the use of cryogenic balloon technology; however, success is critically dependent on a firm contact between the balloon and the PV tissues and a complete occlusion of the PV such that there is no blood flow into the atria around the balloon during the ablation procedure. This can be verified, for example, by injecting dye into the PV via a central lumen in the balloon guidewire. If the dye appears to collect in the vein, it may be assumed that the vein is appropriately occluded. If the vein is not totally occluded and the resulting lesion is not a complete circumferential lesion, i.e., if there is a gap, or if the tissues are only stunned leading to temporary isolation, this results in procedure failure and the need for additional interventions.

It will be appreciated that the J-loop recording/stimulation catheter serves several purposes: (1) it serves as a guide for a balloon ablation catheter to place the balloon in a longitudinal and central position with respect to the desired PV orifice; (2) it anchors the catheter in the vein with the loop positioned in the vein antrum just beyond the orifice; (3) pacing can be applied to the phrenic nerve by the loop electrodes 186 during either RF or cryogenic ablation while the diaphragmatic movement is monitored to insure that the phrenic nerve is not ablated; (4) it allows verification of lesion maturation by monitoring the impedance during cryogenic ablation; and (5) it allows measurement of vein to atria or atria to vein conduction during RF and cryogenic ablation.

Low intensity RF energy may also be applied to the distal balloon ring electrode 188, together with the reference electrode 190 positioned on the balloon catheter shaft just proximal to the balloon (shown in FIG. 8) to measure the conductance across the balloon. If the balloon solidly occludes the PV, the impedance rises and the measurement can also be used to verify PV occlusion. Furthermore, when the system includes a cryogenic balloon, assessment of PV occlusion and assessment of the size of the cryogenic ice ball can also be accomplished by measuring changes in the impedance between the proximal and distal balloon ring electrodes 190 and 188. Since ice is a very poor electrical conductor, as the ice ball totally engulfs the PV, the impedance is seen to rise dramatically and this provides a reliable indicator of PV occlusion and cryogenic lesion maturation.

In the embodiment shown in FIG. 8, the J-loop, equipped with several spaced ring electrodes 186 and thermistors (not shown), is first placed in the vein, as at 196. The J shape anchors the catheter in the vein and the loop is positioned in the vein antrum just beyond the orifice, as shown. The balloon ablation catheter is guided into position by advancing it over the J catheter shaft. Baseline impedance can be measured by the delivery of low power, high frequency electrical current (may utilize less than 1 watt, 550 KHz) to one or more of the electrodes 186 on the J-loop or to the distal ring electrode (188) and the ring electrode 190 that is positioned just proximal to the balloon. This impedance can also be measured by measuring the impedance of the balloon using electrodes 188 and 190. As indicated above, after inflation of the balloon, a second impedance measurement should show an impedance rise if the vein is firmly occluded and no change in impedance will be detected if only partial occlusion is achieved. Additional impedance rise is also recorded with the cryogenic balloon ablation that indicates ice ball formation that engulfs the distal electrode.

The J catheter is preferably a pre-shaped 3-4F catheter that is inserted into the central channel of the ablation balloon. The J portion of the catheter is inserted into a PV with the circular portion of the catheter equipped with ring recording/stimulation electrodes and thermistors that encircle the antrum of the PV. The balloon catheter is advanced over the J catheter using the J catheter as a guidewire. The balloon is positioned to occlude the PV while the circular portion of the catheter encircles the balloon just distal to the balloon contact with the PV. Low power RF energy is applied to the preselected ring electrodes placed either on the balloon shaft or the loop portion of the J catheter for the measurements of impedance pre and post balloon inflation and during the ablation especially with the cryogenic balloon embodiment.

In operation, it should be appreciated that the delivery and tissue contact procedure for both the RF and cryogenic balloon embodiments can be the same. The highly conductive elements and thermistors are circumferentially distributed around the outer surface of both the RF and outer cryogenic balloons.

Figure 9:
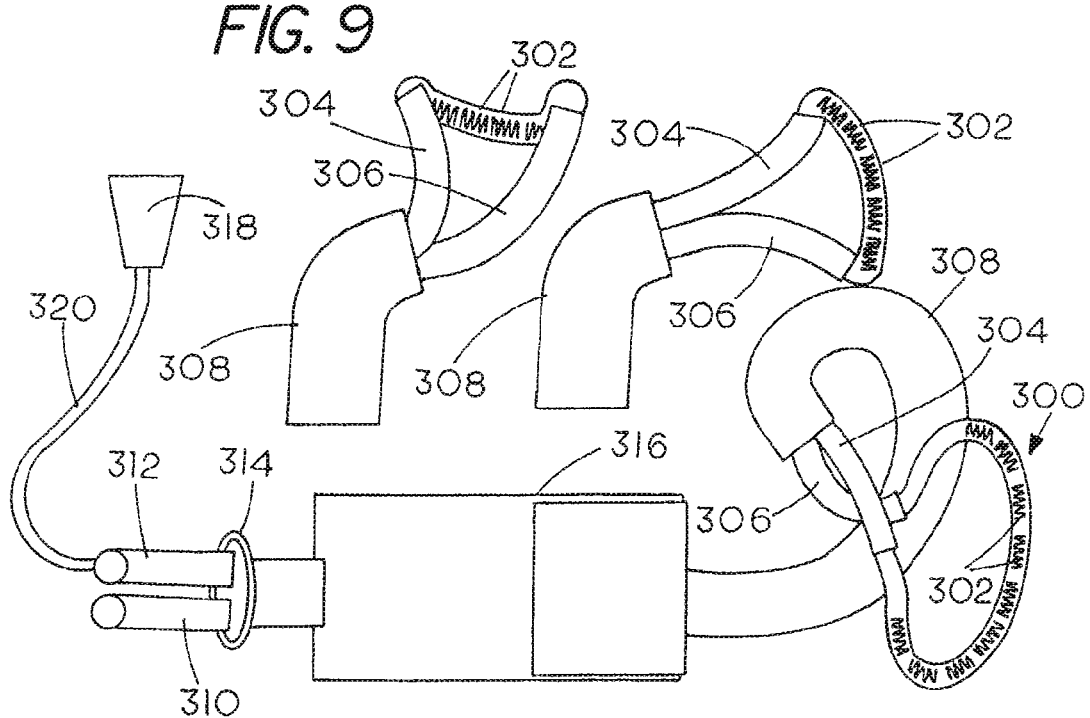
FIG. 9 depicts schematic representations of multi-electrode, loop-type catheters for the creation of linear lesions.

FIG. 9 includes schematic representations of an alternate embodiment of the invention in the form of a multi-ablation electrode-type catheter system for the creation of linear lesions that is particularly designed to create linear lesions in the tissue located between the pulmonary veins to accomplish isolation of these tissues, an aspect which is also deemed very important to the success of atrial fibrillation ablation. As shown in FIG. 9, a flexible multi-electrode ablation catheter 300 containing an array of spaced wire wound ablation electrodes 302 is extended from a support sheath arrangement having two members 304 and 306, which make up a support and torquable ablation catheter support sheath. The catheter support sheath members 304 and 306 are extended from a main transeptal guide sheath 308. Support sheath extensions are shown at 310 and 312 and a locking device for locking the support sheath to a deflectable transeptal guide sheath is shown at 314. A deflection control handle is shown at 316 and an ablation catheter connector is shown at 318, which supplies power to the electrodes 302 via connecting line 320. While other sizes can be used, the flexible multi-electrode ablation catheter 300 is normally 4F and the wire wound electrodes 302 may be 5 mm long with 2 mm gaps in between. Each of the support and torquable catheter guide sheaths 304 and 306 are pre-shaped to allow them to be maneuvered into a pulmonary vein.

Figure 10:
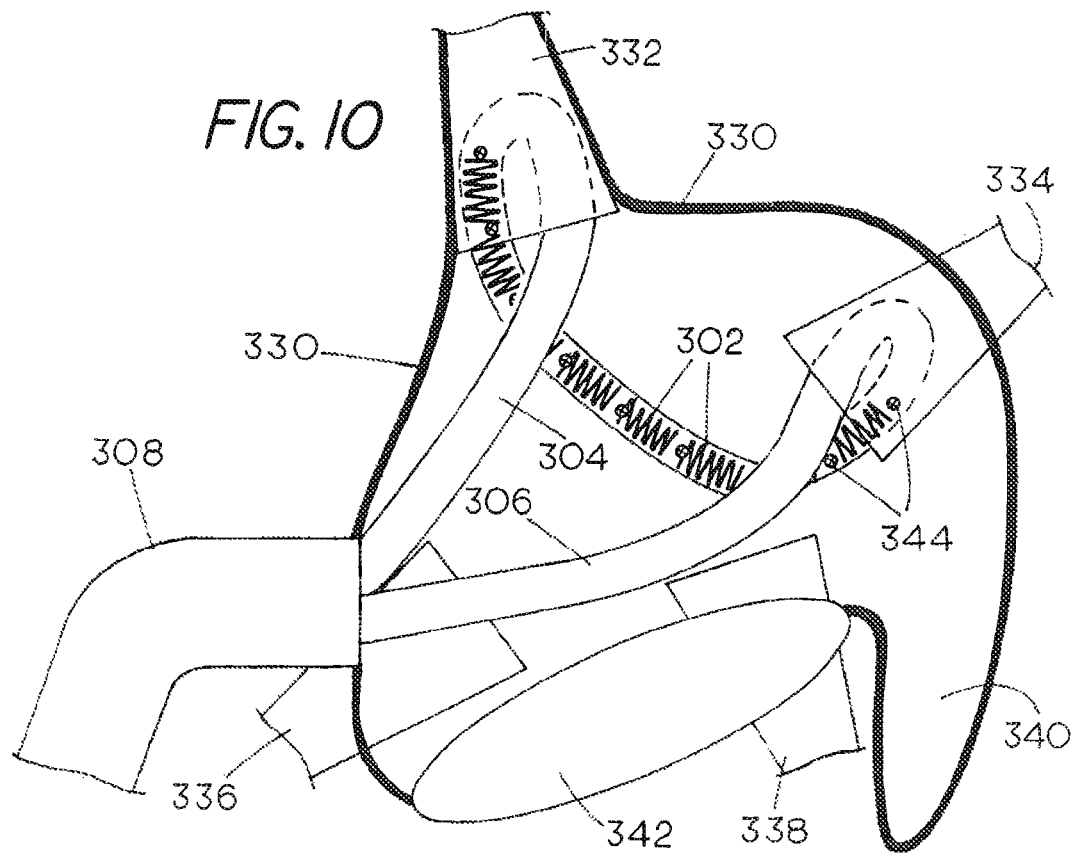
FIG. 10 is a schematic representation of a catheter similar to that of FIG. 9 showing anchoring support sheaths inside pulmonary veins for linear lesion placement between the right superior pulmonary vein (RSPV) and left superior pulmonary vein (LSPV)

The placement of the guide sheaths 304 and 306 in pairs of pulmonary veins is illustrated by the schematic drawings of FIGS. 10-13 in which the left atrial wall is represented by 330 and the pulmonary vein includes RSPV 332, LSPV 334, RIPV 336 and LIPV 338. The left atrial appendage is shown at 340 and the mitral valve at 342 (FIG. 10).

Figure 11:
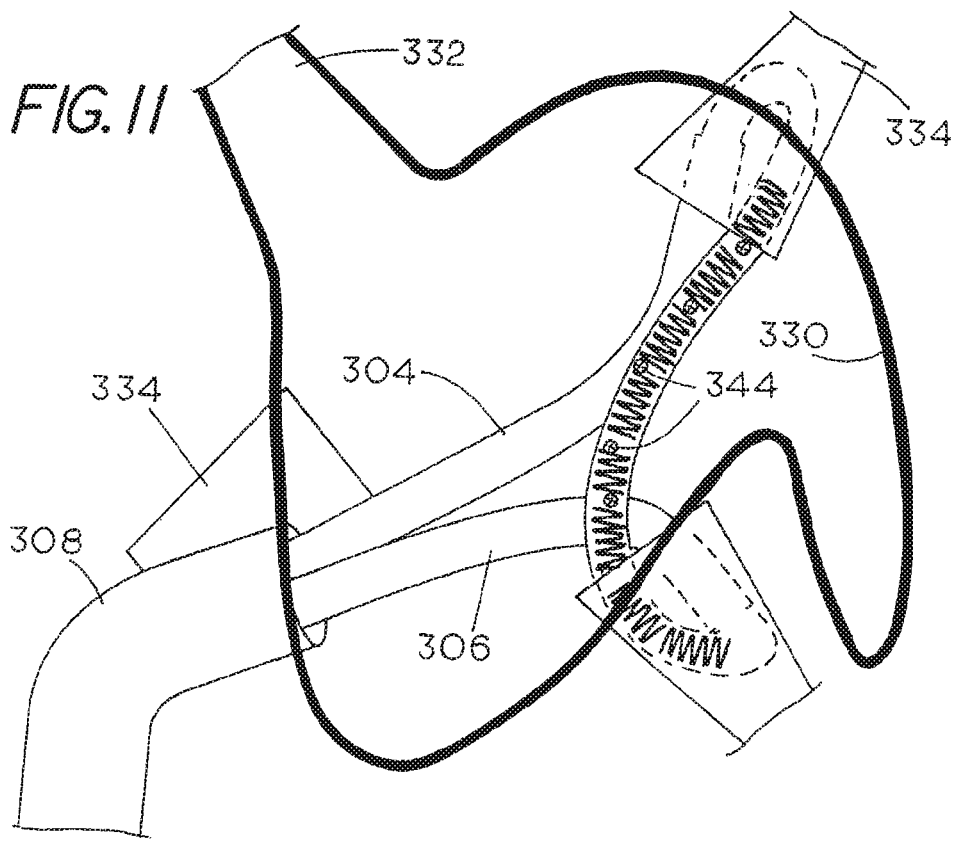
FIG. 11 is a schematic representation similar to that of FIG. 10 for linear lesion placement between left superior pulmonary vein (LSPV) and left inferior pulmonary vein (LIPV)
Figure 12:
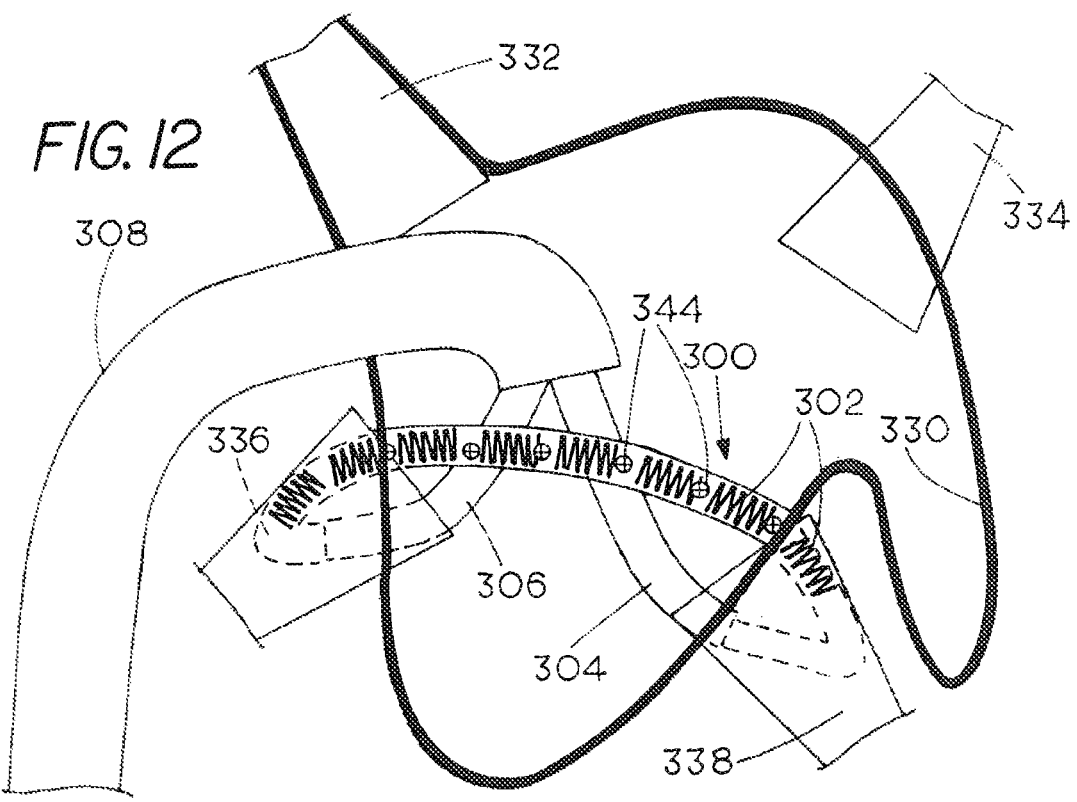
FIG. 12 is a schematic representation similar to that of FIG. 10 for linear lesion placement between left inferior pulmonary vein (LIPV) and right inferior pulmonary vein (RIPV)
Figure 13:
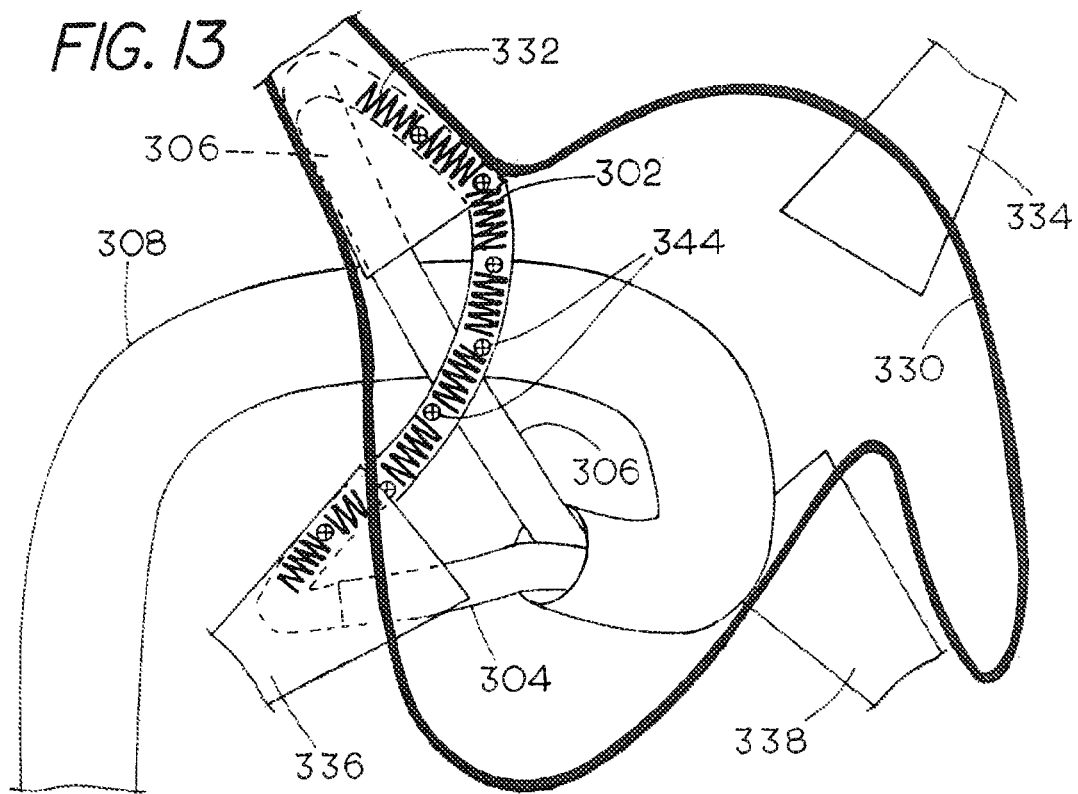
FIG. 13 is a schematic representation similar to that of FIG. 10 for linear lesion placement between right inferior pulmonary vein (RIPV) and right superior pulmonary vein (RSPV)

In this manner, FIG. 10 illustrates how a linear lesion is placed between the right superior pulmonary vein 332 and the left superior pulmonary vein 334. Note that the stabilizing and supporting guide sheaths 304 and 306 provide penetration into the orifices and antrums of the pulmonary veins and also provide support for the array of catheter electrodes. Thermistors as at 344 can be positioned between the ablation/recording electrodes 302. In the same manner, FIG. 11 shows ablation between the LSPV 334 and LIPV 338. FIG. 12 shows ablation between the LIPV 338 and the RIPV 336. Finally, FIG. 13 illustrates ablation between the RSPV 332 and the RIPV 336.

Figure 14:
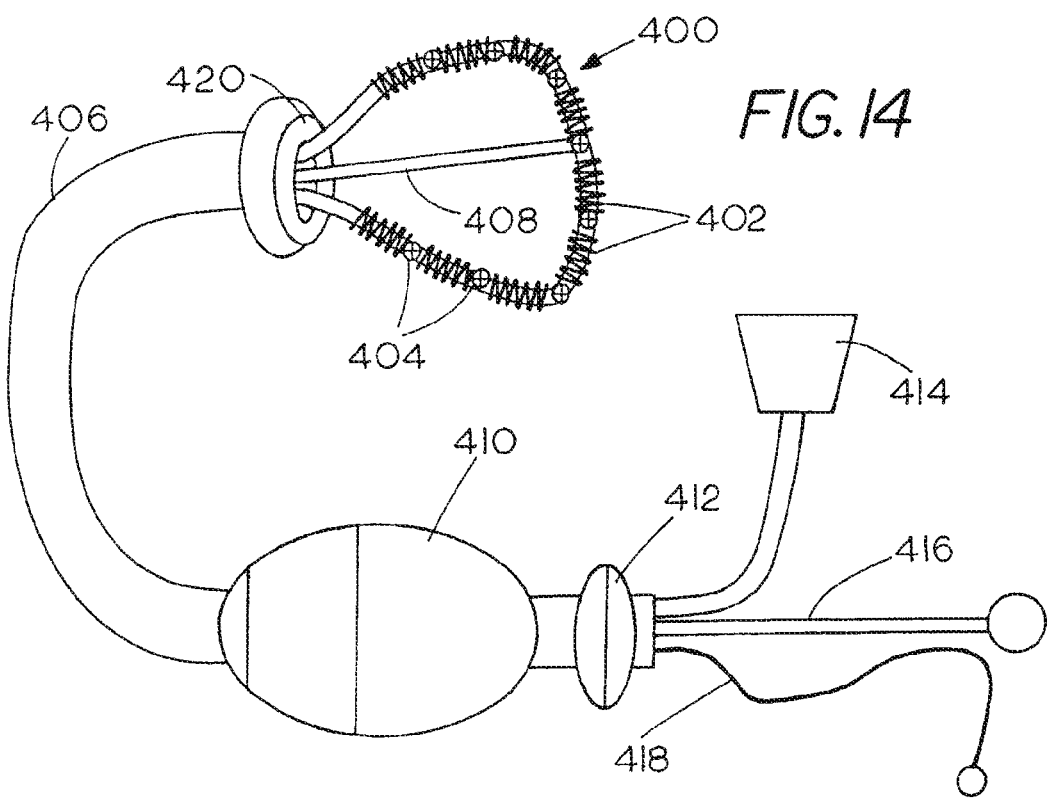
FIG. 14 is a schematic representation of an alternate embodiment of a multi-electrode loop-type catheter which includes an insulated extension rod.
Figure 15:
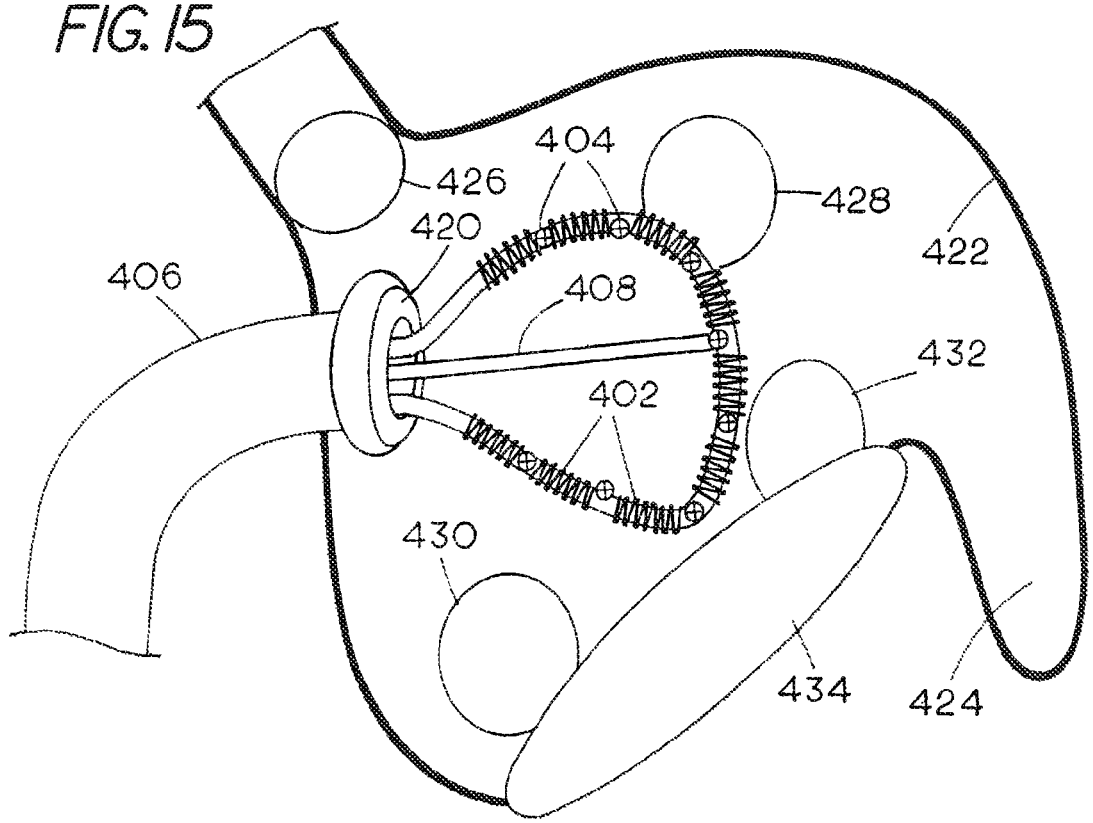
FIG. 15 illustrates the multi-electrode catheter of FIG. 14 as it might be used to create linear lesions between pulmonary veins.

Thus, the flexible multi electrode ablation catheter 300 is placed in a pair of stiffer guide sheaths 304 and 306 which, in turn, are placed in a deflectable guide sheath 308, which is a transeptal device. In operation, once the main sheath is advanced into the desired chamber, the ablation catheter 300 and the two support guide sheaths 304 and 306 are advanced out of the main sheath into the chamber. Each of the supporting guide sheaths 304 and 306 are pre-shaped to allow them to be maneuvered into a pulmonary vein. The supporting sheaths 304 and 306 can be advanced individually by pushing and/or rotating the proximal portion in and out of the main deflectable sheath 308. The position of the supporting sheaths can be locked in place by releasing or securing the locking mechanism 314 on the deflection control handle 316. Good ablation catheter contact with the desired tissues is ensured once the support sheaths are forced into the desired pulmonary veins while keeping the ablation catheter taut across the tissues, as illustrated in the figures. Another embodiment is seen schematically in FIGS. 14 and 15. That embodiment is in essence a simplified version of the embodiment shown in FIGS. 9-13 in which a multi-electrode catheter 400 with wire wound ablation and measurement electrodes 402 and intermediate thermistors 404 is inserted directly into the main deflectable guiding sheath 406 to form a loop at the end of the sheath. An extension rod, shown at 408, is used to modify the shape of the loop. A handle and deflection control is shown at 410 with locking device 412 and multi-electrode and thermistor connector is shown at 414. An extension rod control is shown at 416 and a draw string with stopper at 418. A septum protection balloon is shown at 420. In FIG. 15, the left atrial wall is shown at 422 with the left atrial appendage at 424. The pulmonary vein orifices are shown at 426, 428, 430 and 432 and the mitral valve at 434. The draw string or pull wire at 418 can be used to minimize the size of the main guiding sheath 406 by enabling retraction of the ablation catheter 400 inside the orifice of the main deflectable guiding sheath prior to deployment. It should be noted that the insulated extension flexible rod 408 provides further support and stability to the catheter loop and improves tissue contact. Catheter mobility and position can be accomplished as desired by deflecting the main sheath in rotation, ablation catheter torque extension and expansion of the catheter loop, extension or retraction of the insulated rod 408.

Figure 16:
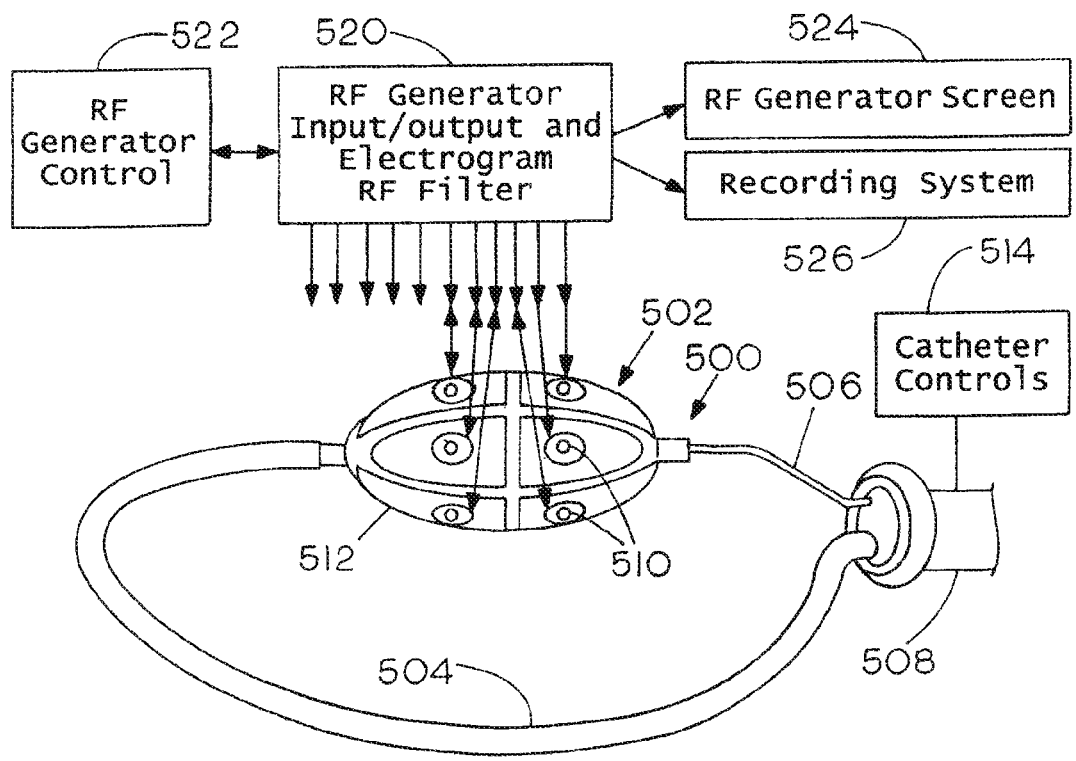
FIG. 16 is a schematic and partial block diagram of an ablation control system.

FIG. 16 is a schematic representation of a monitoring and control system for an RF ablation system in accordance with the invention. The system includes a catheter system 500 with a balloon catheter 502 mounted on catheter shaft 504 which rides over guidewire 506. A sheath is shown at 508. The balloon catheter includes a plurality of thermistor and recording electrodes 510 and RF ablation electrodes 512. The catheter further includes mechanical manipulation controls and liquid inflation and circulation controls represented by block 514.

An RF energy power generator system including input and output data processing and an electrogram RF filter is shown at 520 with connection to RF control system 522. The RF generator is connected to a visual output or screen display device as shown in block 524 and a recording system is shown connected at 526.

The RF power generator is programmed to control and modulate RF power to each ablation electrode in any of the multi-electrode RF catheter systems as each electrode is separately connected and separately controllable. The delivery of power is controlled so that only the electrodes that are in firm contact with the targeted tissue are energized and the desired power is carefully controlled to avoid overheating blood or ablated tissue. Overheating of ablated tissue may cause char formation and can lead to stroke. Thus, each independent power source is modulated based on sensed temperature and the first derivative of the temperature change (dT/dt) which describes the rate of temperature rise. Real time local electrical activity is closely monitored. This includes recording of electrogram amplitude, changes in maximal frequency of the local electrogram and impedance changes.

Once RF power is turned on, the power generator system modulates the RF power in accordance with a pre-programmed procedure, which may be as follows:
1. After contact and tissue viability is defined within acceptable parameters, e.g.,
   a. Local electrogram>1 mV,
   b. Maximum electrogram frequency>8 Hz,
   c. Impedance<180 ohms.
   Starting with a low power setting, power is increased to control electrode temperature rate of change at a preset level such as 5° C./second=dT/dt;
2. Achieve maximum preset temperature such as 65° C.;
3. Terminate power input if impedance increases above a preset level (150-180 ohms, for example) or if the local electrogram decreases by 50% or more from baseline levels, and/or in conjunction with the electrogram amplitude, if the local electrogram frequency decreases by, for example, 30% from the baseline value.
4. Certain values in items 3 can be overridden if advisable during the procedure.
5. Reduce power to minimum when successful ablation is indicated by electrogram data and impedance measurements.

The RF power generator system is designed to receive data related to all of the necessary parameters from the ablation electrodes and thermistors, including local electrogram amplitude and percent change, maximum electrogram frequency temperature, rate of change of temperature (dT/dt) impedance, output power and application time.

After data received indicates that local tissue has been successfully ablated and power has been terminated, the catheter can be repositioned for the next local tissue ablation.

Figure 17:
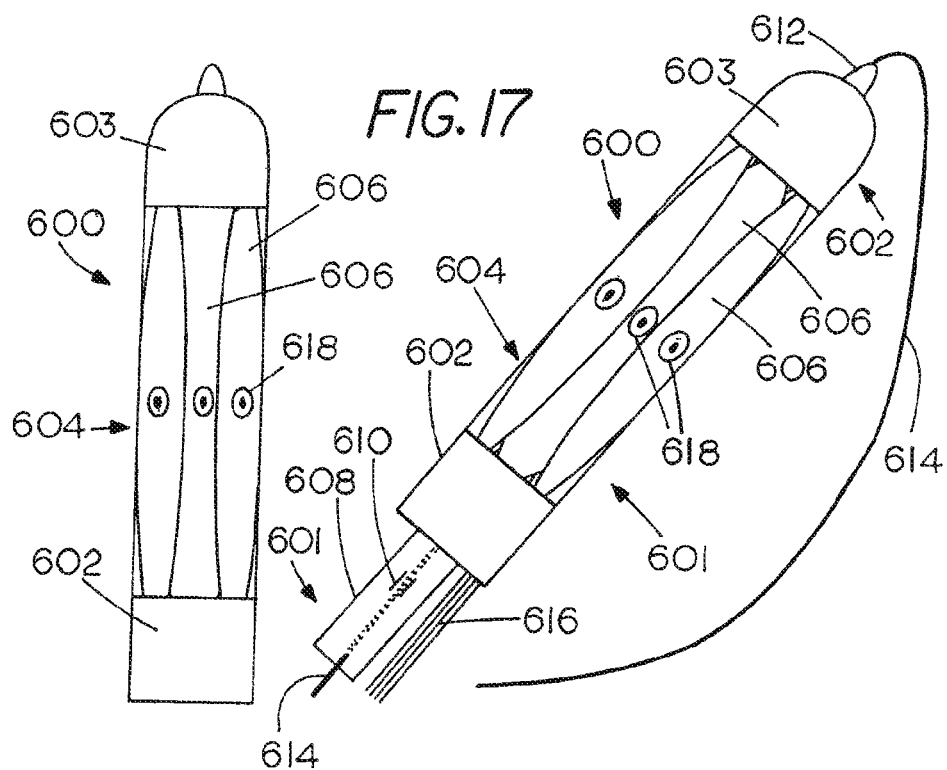
FIG. 17 is a schematic representation of another embodiment of an RF balloon ablation device with the balloon in a collapsed state and parts removed for clarity.
Figure 20A:
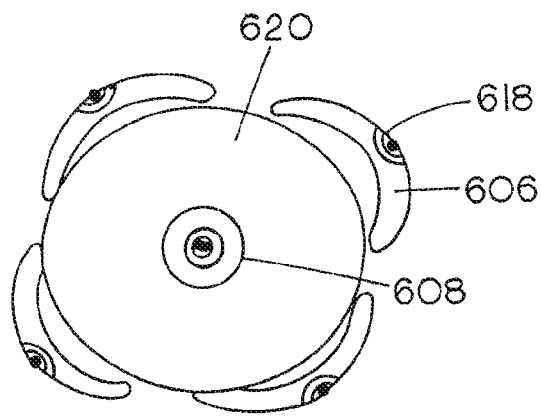
FIGS. 20A and 20B are schematic cross-sectional views through the balloon of FIG. 17.
Figure 20B:
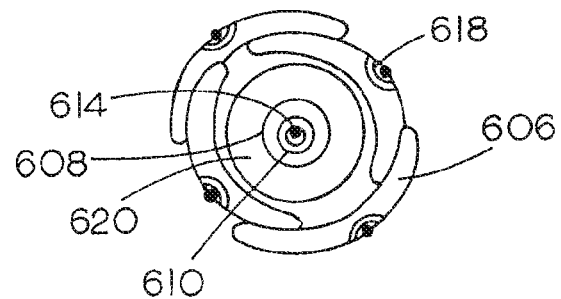

Another embodiment of an RF balloon ablation catheter device is shown generally at 600 in FIG. 17 with the balloon in a fully collapsed state. The device includes an outer tubular member, guide catheter or guide sheath shown with segments 602 and 603. The guide catheter or sheath includes an expandable or balloon section 604 therebetween. Expandable section 604 is provided with conductive electrode ablation elements 606 which are connected between shaft segments 602 and 603. The electrode elements are preferably in the form of conductive ribbon shapes which are mounted outside of and are independent of an inner expandable balloon device 620. As seen best in FIGS. 20A and 20B, the electrode elements overlap when the expanding section of the device 604 is in the collapsed or stored position as shown in FIG. 20B and are slightly separated when the balloon device 620 is expanded as shown in FIG. 20A. In this manner, the expanding or balloon device can be used to control the diameter described by the deployed ablation device elements. Although those figures depict four electrode elements, any suitable number can be used. The elements are all separately connected and include devices for ablation, temperature and electrical activity monitoring.

The outer catheter shaft contains additional internal concentric hollow tubes, including an intermediate tubular member 608 and an innermost tubular member 610. The innermost tube 610 connects to the tip of the catheter 612 and contains an axially adjustable guidewire 614. These are shown exposed in FIG. 17. Tubular member 610 also provides a path that enables fluid designed to be injected in a procedure to be conducted from the catheter handle and delivered through the catheter. The slightly larger intermediate tubular member 608 connects with the interior of the expanding balloon device 604 and provides a path for inflating fluid. The outer tube or catheter shaft member contains wires as at 616 which connect to the ablation elements and also to thermistor elements and recording electrodes which are imbedded in the ablation elements 606 as at 618.

Figure 18A:
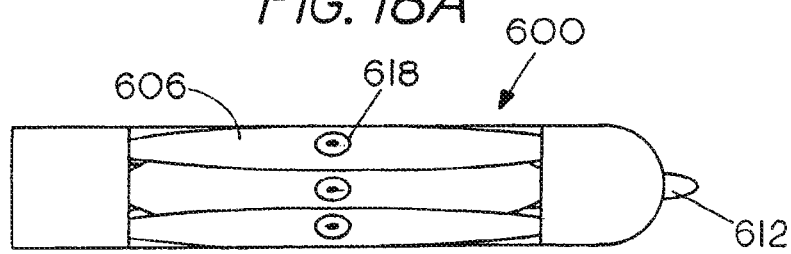
FIGS. 18A and 18B compare the ablation device of FIG. 17 with the balloon in a collapsed and in an expanded state, respectively.
Figure 18B:
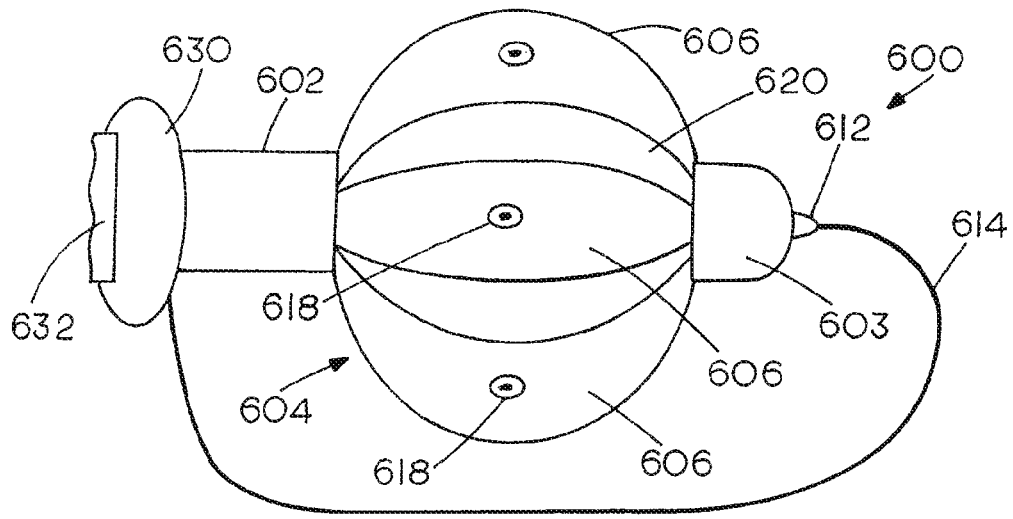

FIGS. 18A and 18B show a comparison of the hollow ablation device 600 showing the expanding or balloon device in the collapsed and expanded state, respectively. As best shown in FIG. 20B, the ribbon electrode elements 606 overlap when the balloon section 604 is in the deflated or stored position and, conversely, in the expanded state, the electrodes as shown in FIGS. 18B and 20A are slightly separated by the expansion of the balloon and a small amount of balloon material 620 is exposed. This enables a maximized ablation electrode surface to be exposed, yet allows individual operation of the ablation elements. This configuration enables peripheral ablation in a pulmonary vein, for example, with a single placement of the balloon device. The ribbon ablation elements should be configured such that, after a procedure, when the balloon device is collapsed or deflated, the ablation elements reassume the overlapping configuration and that no sharp edges appear or are exposed that could adversely affect adjacent tissue. As the ends of the ribbon electrodes 606 are fixed between the segments 602 and 603, the distance between these elements is reduced as the balloon material 620 is expanded, as elements of the system ride independently on the guidewire 614. Certain embodiments can be made so that the shaft deflects as the balloon expands if a more rigid construction is desired.

Figure 19:
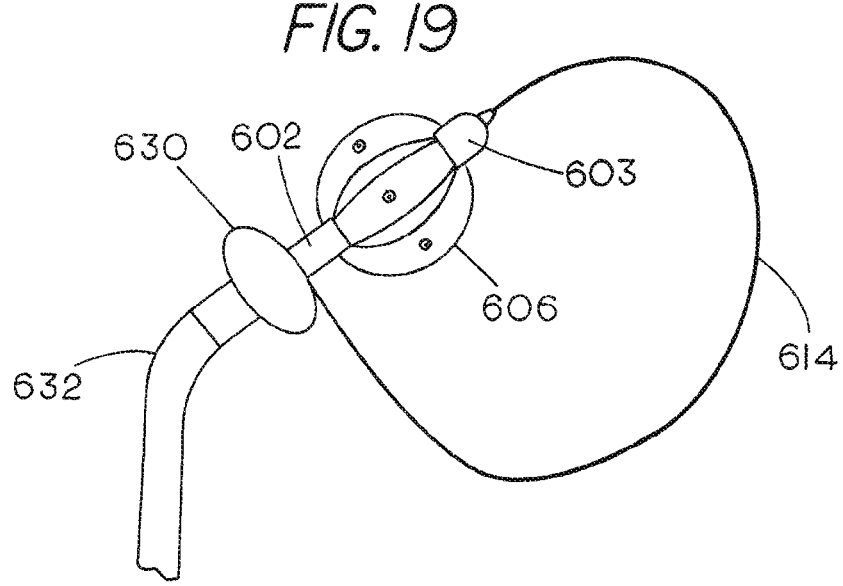
FIG. 19 is a fragmentary or partial view of a catheter device, including the balloon ablation device of FIG. 17.

As shown particularly in FIGS. 18B and 19, the balloon ablation catheter device further includes a septal protection balloon 630 and an additional guiding sheath segment is shown at 632. As with previously described embodiments, this device is designed to penetrate the septal tissue and the inflation of the balloon 630 during a procedure prevents the guiding sheath 632 from being pushed back through the septal tissue and possibly causing damage to the septum. Generally, where the ablation in the left atrium is involved, the guiding sheath is used to penetrate the septum from the right atrium into the left atrium. As shown in FIGS. 18B and 19, as with previously described embodiments, the guidewire loop formed by the guidewire 614 in a chamber such as the left atrium provides a stable track for the ablation balloon to be placed in sequential steps to create a linear lesion about the periphery of the chamber, as desired. This balloon device can be advanced over the guidewire, as desired, during a procedure. Controls, such as shown for previous embodiments, including the handle control shown in FIG. 3, may be used for any embodiment.

Alternate configurations are depicted in FIGS. 21A, 21B and 22A, 22B. In FIGS. 21A and 21B there is shown an RF balloon ablation catheter 700 of similar construction to that of FIG. 17 that includes a catheter shaft with spaced catheter shaft elements 702 and 703, spanned by connected ribbon ablation elements 706 outside of an expanding portion 704. These elements are also provided with imbedded thermistor and recording electrodes as at 718. The remaining structure and components are similar to those in FIG. 17 and include concentric tubular members 708 and 710, which accomplish the same functions as element 608 and 610 in the embodiment of FIG. 17. In this embodiment, the ribbon electrode elements 706 are arranged in a spiral pattern about the periphery of the expanding balloon ablation section 704. A criss-crossed pattern is shown at 704B in FIG. 21B.

In yet another, similar embodiment depicted in FIGS. 22A and 22B, there is shown an RF balloon ablation catheter device 800, which includes a pattern of ribbon electrodes 806 that are also arranged as a lattice or criss-crossed pattern in which the separate ablation elements or electrodes are insulated from each other. The catheter also includes segments 802, 803 and 804. A guidewire tube is shown at 808 and a guidewire at 814. The ablation elements are also provided with imbedded thermistor and electrical activity recording elements at 818. This pattern also assures a full circumferential ablation, as in a pulmonary veins orifice. The device is shown both in the collapsed or deflated and expanded or inflated states in the figures.

While many sizes are possible, the ribbon-type ablation elements are typically about 30 mm long by 3 mm wide and may be elliptical in shape. The balloon ablation catheter should be about 20 mm in diameter when fully expanded and about 11F (3.6 mm) in the deflated or stowed state. The guiding or deployment sheath is about 12F (3.9 mm). The balloon and electrodes may be of any suitable material that is also biocompatible and such materials are well known.

From the above description and drawings, it will be apparent that there is a unique nature associated with the present invention that resides in the functionality of the embodiments to accomplish precise and excellent ablation, particularly with regard to the control of atrial fibrillation in the human heart. It will be appreciated, however, that the devices and techniques can be applied in any area of the heart. Thus, it can be applied to the right and left ventricle as well as for mapping and ablation of ventricular tachycardia. With respect to atrial fibrillation, it has been found that the catheter systems in accordance with the present invention have vastly improved the contact and catheter tractability leading to more predictable lesions while minimizing the amount of tissue that is ablated.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A device for ablating tissue in a body organ chamber, including heart chambers, comprising:
   (a) a guide body or sheath having a deflectable distal end portion;
   (b) an independent axially adjustable guidewire extendable from said distal end portion of said guide body to selectively form a guidewire loop that is controllable to create forced contact with organ chamber tissue in a variety of positions and anatomical locations;
   (c) an ablation section in said guide body including an inflatable expanding device, able to travel over said guidewire;
   (d) wherein said inflatable expanding device is in the form of a balloon and includes a plurality of ribbon-type outer conductive ablation elements separate from and disposed about the external periphery of said inflatable expanding device in a manner such that they overlap when the inflatable expanding device is deflated or collapsed and wherein said ablation elements separate from contacting each other when said inflatable expanding device is inflated.

2. A device for ablating tissue as in claim 1 wherein said inflatable expanding device is part of and connects segments of said guide body or sheath which travel along said guidewire.

3. A device for ablating tissue as in claim 2 wherein each of said plurality of ribbon-type conductive ablation elements includes sensors to monitor temperatures and localized electrical activity.

4. A device for ablating tissue as in claim 2 further comprising a control mechanism for locking said guidewire loop and for selectively advancing and retracting said inflatable expanding device along said guidewire loop to allow for tissue contact and the creation of continuous lesions.

5. A device for ablating tissue as in claim 1 wherein each of said plurality of conductive ablation elements includes a device to monitor temperature and electrical activity.

6. A device for ablating tissue as in claim 1 wherein said plurality of ribbon-type conductive ablation elements are arranged in a spiral pattern.

7. A device for ablating tissue as in claim 1 wherein said plurality of ribbon-type conductive ablation elements are arranged in a criss-crossed pattern to enhance a circumferential ablation pattern.

8. A device for ablating tissue as in claim 7 wherein each of said plurality of ribbon-type conductive ablation elements includes sensors to monitor temperatures and electrical activity.

9. A device for ablating tissue as in claim 1 further comprising a control element for selectively advancing and retracting said inflatable expanding device along said guidewire loop to allow for tissue contact and the creation of continuous lesions.

10. A device for ablating tissue as in claim 9 wherein said control element includes a pull wire.

11. A device for ablating tissue as in claim 1 wherein said guide body further comprises an inflatable guide body balloon located at the distal portion thereof for preventing the guide body from retracting back through a penetrated chamber wall during a procedure.

12. A device for ablating tissue as in claim 1 comprising a control element that further comprises a mechanism for locking said guidewire loop and allowing controlled movement of the inflatable expanding device over the guidewire.

13. A device for ablating tissue as in claim 1 wherein said ablation elements use radio frequency to ablate tissue.

14. A device for ablating tissue as in claim 1 wherein said inflatable expanding device includes a cooling mechanism.

15. A device for ablating tissue as in claim 14 wherein said cooling mechanism includes a system for circulating cooling liquid inside said balloon at a desired pressure.

16. A device for ablating tissue as in claim 1 wherein said plurality of ribbon-type conductive ablation elements resume an overlapping configuration when said balloon is collapsed after inflation.

* * * * *